(12) United States Patent
Wittwer et al.

(10) Patent No.: US 6,503,720 B2
(45) Date of Patent: *Jan. 7, 2003

(54) METHOD FOR QUANTIFICATION OF AN ANALYTE

(75) Inventors: Carl T. Wittwer, Salt Lake City, UT (US); Martin Gutekunst, Eberfind (DE); Sabine Lohmann, Iffeldorf (DE)

(73) Assignees: Roche Diagnostics GmbH (DE); University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/789,170

(22) Filed: Feb. 20, 2001

(65) Prior Publication Data

US 2002/0028452 A1 Mar. 7, 2002

Related U.S. Application Data

(63) Continuation of application No. 09/281,448, filed on Mar. 30, 1999, now Pat. No. 6,303,305.

(51) Int. Cl.[7] ........................... C12Q 1/68; C12P 19/34; C07H 21/04; C07H 21/00
(52) U.S. Cl. ........................... 435/6; 435/91.2; 435/39; 536/24.3; 536/25.32
(58) Field of Search ........................... 435/6, 91.2, 39; 536/24.3, 25.32

(56) References Cited

U.S. PATENT DOCUMENTS

| | | | | |
|---|---|---|---|---|
| 4,683,195 A | | 7/1987 | Mullis et al. ................... | 435/6 |
| 4,683,202 A | | 7/1987 | Mullis ........................... | 435/91 |
| 5,118,801 A | | 6/1992 | Lizardi et al. ................. | 536/27 |
| 6,303,305 B1 | * | 10/2001 | Wittwer et al. ................. | 435/6 |

FOREIGN PATENT DOCUMENTS

| | | | | |
|---|---|---|---|---|
| WO | WO 91/02814 | 3/1991 | ............ | C12Q/1/68 |
| WO | WO 97/46707 | 12/1997 | ............ | C12Q/1/68 |
| WO | WO 97/46712 | 12/1997 | ............ | C12Q/1/68 |
| WO | WO 97/46714 | 12/1997 | ............ | C12Q/1/68 |

OTHER PUBLICATIONS

T. Kohler et al., "Quantitation of mRNA by Polymerase Chain Reaction: Nonradioactive PCR Methods," Springer Lab Manual, Chapter 1.1.1, pp. 3–14, Springer–Verlay Berlin Heidelberg (1995).

Wittwer, et al., "Continuous Fluorescence Monitoring of Rapid Cycle DNA Amplification," *Bio Techniques*, vol. 22, pp. 130–138 (Jan. 1997).

Wittwer, et al., "The LightCycler: A Microvolume Multisample Fluorimeter with Rapid Temperature Control," *Biotechniques*, vol. 22, pp. 176–181 (1997).

Bernard et al., , "Integrated Amplification and Detection of the C677T Point Mutation in the Methylenetetrahydrofolate Reductase Gene by Fluorescence Resonance Energy Transfer and Probe Melting Curves," *Analytical Biochemistry* 255, pp. 101–107 (1998).

Wiesner, R.J., "Direct Quantification of Picomolar Concentrations of mRNAs by Mathematical Analysis of a Reverse Transcription/Exponential Polymerase Chain Reaction Assay," *Nucleic Acids Research*, vol. 20, No. 21, pp. 5863–5864 (1992).

Higuchi et al., "Kinetic PCR Analysis: Real–Time Monitoring of DNA Amplification Reactions," *BioTechnology*, vol. 11, pp. 1026–1030 (Sep. 1993).

Haendler, et al., "Complementary DNA for Human T–Cell Cyclophilin," *The EMBO Journal*, vol. 6, No. 4, pp. 947–950 (1987).

Shirai, et al., "Cloning and Expression in *Escherichia coli* of the Gene for Human Tumour Necrosis Factor," *Nature*, vol. 313, pp. 803–806 (Feb. 28, 1985).

Siebert, P.D., "Quantitative RT–PCR,", Methods in Molecular Medicine, vol. 13: *Molecular Diagnosis of Infectious Diseases*, Chapter 4, pp. 55–79 (1998).

* cited by examiner

*Primary Examiner*—Gary Benzion
*Assistant Examiner*—Joyce Tung
(74) *Attorney, Agent, or Firm*—Barnes & Thornburg

(57) ABSTRACT

Methods are provided for quantifying the concentration of a nucleic acid in a nucleic acid sample. The methods include contacting the nucleic acid sample with an amplifying agent, amplifying at least one predetermined locus of the nucleic acid by subjecting the sample to a number of amplification, generating an amplification curve or array, calculating the first, second or n th order derivative of the amplification curve or array, determining a maximum, minimum, or zero value of the derivative, and using the maximum, minimum, or zero value to calculate the initial concentration of the nucleic acid in the nucleic acid sample.

22 Claims, 14 Drawing Sheets

METHOD FOR QUANTIFICATION OF AN ANALYTE

This application is a continuation of U.S. patent application Ser. No. 09/281,448, now U.S. Pat. No. 6,303,305 filed Mar. 30, 1999.

FIELD OF THE INVENTION

The present invention relates to the quantification of analytes which are present in low concentrations but can be amplified or replicated under suitable conditions. In particular, it relates to quantification of a specific polynucleotide sequence within a sample containing polynucleotides.

BACKGROUND OF THE INVENTION

Among the number of different analytical methods that detect and quantify nucleic acid sequences, Polymerase Chain Reaction (PCR) has become the most powerful and wide-spread technology, the principles of which are disclosed in U.S. Pat. No. 4,683,195 and U.S. Pat. No. 4,683,102 (Mullis et al.). However, a typical PCR reaction by itself only yields qualitative data, since, after a phase of exponential or progressive amplification, the amount of amplified nucleic acid reaches a plateau, such that the amount of generated reaction product is not proportional to the initial concentration of the template DNA.

As a consequence, many different PCR based protocols have been developed in order to obtain reliable and reproducible quantitative data. Generally, two different basic principles can be discriminated:

i) Competitive PCR using internal standards ii) Quantification of target DNA by initial generation of a calibration curve, reviewed by Siebert, in: Molecular Diagnosis of infectious diseases (ed. Reiscbl, Humana Press, Totowa, N.J., p. 55–79 (1998).

A major improvement in the generation of quantitative data derives from the possibility of measuring the kinetics of a PCR reaction by On-Line detection. This has become possible recently by means of detecting the amplicon through fluorescence monitoring. Examples of such techniques are disclosed in detail in WO 97/46707, WO 97/46712 and WO 97/46714 (Wittwer et al.), the disclosures of which are hereby incorporated by reference.

Prior to the availability of On-Line PCR-detection, Wiesner et al. (Nucl. Acids Res. 20, 5863–5864 (1992)), for the first time used data from multiple cycles of a PCR reaction, wherein after each cycle, the product concentration was assayed by radioactive incorporation and subsequent scintillation counting. For each curve, the initial template concentration ($N_o$) and amplification efficiency (eff) were determined by linear regression of data points on a product concentration (Nn) versus cycle number graph as defined by the following formula:

$$\text{Log } Nn = (\log \text{eff}) n + \log N_o.$$

Higuchi et al. (BioTechnology 11, 1026–1030 (1993)) were the first to disclose a simpler approach for initial template quantification using fluorescence monitoring at each cycle. A fluorescence threshold level was used to define a fractional cycle number related to initial template concentration. Specifically, the log of the initial template concentration is inversely proportional to the fractional cycle number (CT), defined as the intersection of the fluorescence versus cycle number curve with the fluorescence threshold.

In a more sophisticated embodiment of the fluorescence threshold method, the threshold level is not chosen manually or arbitrarily, but is set to three times the coefficient of variation of the signals which are obtained as fluorescent background noise.

However, there exist several major draw backs of the referenced prior art. First of all, prior art methods require corrections for different fluorescent background signals in order to compensate for sample to sample variations due to differences in excitation or emission efficiencies. Secondly, since quantification of template dependent amplification always has to be performed during the log linear phase of the reaction (Köhler et al., "Quantitation of mRNA by PCR: Nonradioactive methods, p. 6 Springer Berlin 1995, ed. Köhler), a log linear window of the reaction has to be determined by the user prior to the actual quantification experiment. In addition, the setting of a threshold level requires an experienced experimental person skilled in the art, since it is chosen manually without taking specific preconditions of the experiment to be performed into account.

Thus, there exists a requirement for methods, wherein the concentration of an amplifiable or replicable analyte may be determined without correction for different fluorescent background, independently from a user defined log phase and a user defined threshold level, and wherein at the same time the determined concentration is independent of the absolute level of signal which is generated in the plateau phase of the reaction. Moreover, such an independence of absolute signal level is also advantageous for systems, wherein multiple fluorescent signals being detected through multiple channels with different window ranges may be compared.

SUMMARY OF THE INVENTION

The present invention describes methods for quantitatively analyzing either an amplifiable or a self replicating system in such a way that the amount of amplification or self replication product is measured continuously. In accordance with one embodiment of the present invention a method for quantifying an analyte is provided. The method comprises the steps of contacting the analyte with an amplifying agent, and amplifying at least one predetermined locus of the analyte. The amount of amplification product is then determined as a function of reaction time and the first, second or n th order derivative of said function is calculated wherein n is a natural number. The maximum, the zero value or the minimum of said derivative is then determined and the initial concentration of the analyte is calculated from said maximum, zero value or minimum. The disclosed method can also be used to quantitatively analyze the growth rate of organisms and thus measure the effect of a modified environmental condition on the growth of an organism.

BRIEF DESCRIPTION of the DRAWINGS

FIG. 3B, 2/4/2; FIG. 3C, 3/3/3; FIG. 3D, 3/4/3; FIG. 3E, 4/3/2; FIG. 3F, 4/4/2; FIG. 3G, 6/3/2; FIG. 3H, 6/4/2; FIG. 3I, 6/5/2; FIG 3J, 6/6/2.

FIG. 4: Graphic representation of the fractional cycle number determination by quadratic estimation of the 2nd derivative maximum.

FIG. 6: Graphic representation of the growth curves generated for a population of bacteria cells cultured in the presence of substance A (A), substance B (B) substance C (C) and the control (T).

Detailed Description of the Invention

Figure 1A:
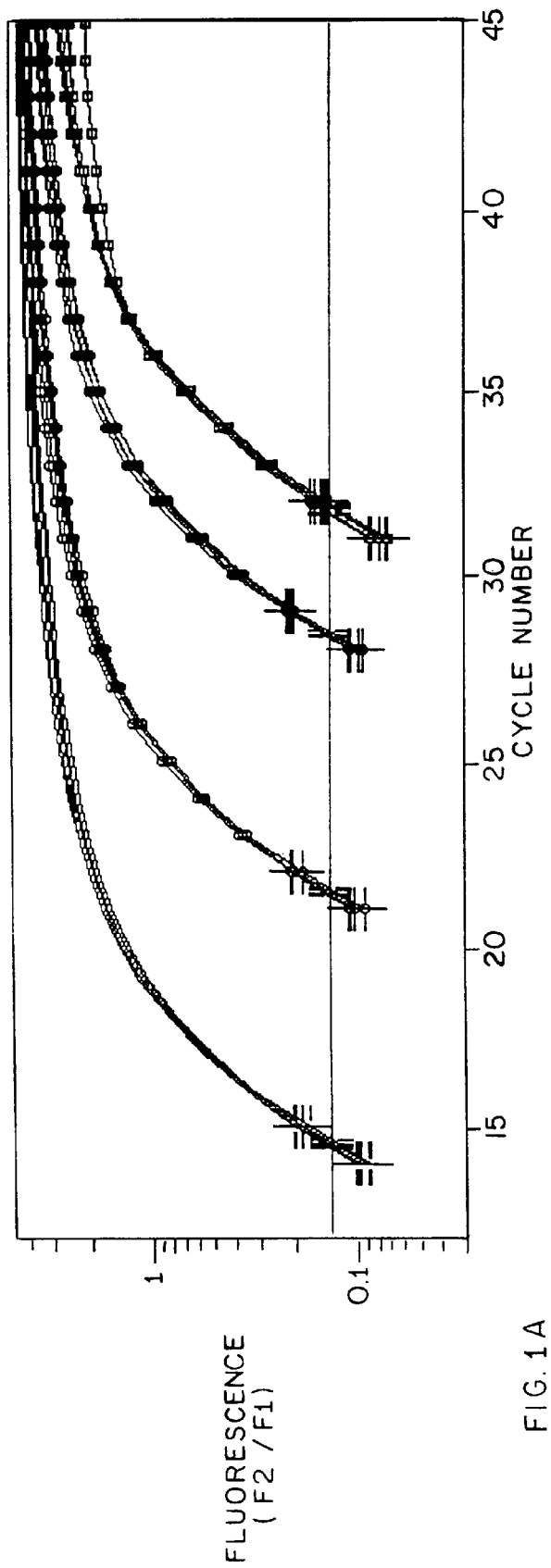
FIG. 1A: Measurement of fluorescence signal with FRET-HybProbes.

The invention comprises methods for quantitatively analyzing either an amplifiable or a self replicating system in such a way that the amount of amplification or self replication product is measured continuously. Continuous measurement in a PCR reaction, for example, may also mean that measurements are performed once each cycle. The method of the present invention is especially applicable for embodiments, wherein during one phase of the amplification reaction or self replication (usually starting from the beginning or alternatively after an initial lag phase) the amount of the target product increases progressively. Moreover, the method is applicable for embodiments wherein after said exponential phase, the rate of amplification decreases.

By using appropriate mathematical algorithms, the generated data can then be used to set up a mathematical function, which discloses the smoothened kinetics of signal generation at different time points. In order to obtain a function, from which derivatives can be calculated, it is possible for example to perform a polynomial fit thereby creating a data set which reflects the smoothened kinetics of the originally measured raw data. It has been proven to be advantageous for the present method, if the polynomial fit is calculated by a Savitzky Golay filter (Press et al., in: Numerical Recipes in C, the art of scientific Computing, Cambridge University Press, second edition, p. 650 ff). From such a function, first, second or even higher order derivatives can be calculated and the maximal, minimal or zero values of said functions can be determined. The obtained data are characteristic parameters for each amplification or self replication and can be used either to quantify the original amount of amplified entity or the influence of compounds or environmental factors (such as temperature, pH, electromagnetic radiation, or nutrient composition) which are present during amplification or self replication of the sample.

The majority of amplifiable or self replicating systems work in a way that amplification or self replication over a certain period of time is obtained exponentially, which is usually the case at the very beginning of the reaction. However, in case of growth curves of microorganisms or cell populations, for example, there may exist a lag phase at the beginning, which at a later time point may enter an exponential phase. However, this does not affect the applicability of the invention for such embodiments.

As outlined above, one embodiment of the invention involves the quantification of specific nucleic acid sequences, which are present in low amounts in a sample to be analyzed and may be amplified or self replicated using appropriate amplification methods. The most common amplification method for nucleic acid analytes is the polymerase chain reaction (PCR), which is well-known for persons skilled in the art. A summary of basic applications is given in Siebert, Molecular Diagnosis of infectious diseases (ed. Reiscbl, Humana Press, Totowa, N.J., p. 55–79 (1998)). Within the scope of the invention, however, are also different methods of amplifying nucleic acids, for example NASBA (Malek et al., WO 91102814). The target nucleic acid may either be double-stranded DNA, single-stranded DNA or any type of RNA. In the latter case, prior to PCR, a cDNA synthesis using standard protocols may be performed.

In accordance with one embodiment, a method for quantifying an analyte is described, wherein the analyte is a polynucleic acid. The method comprises the steps of contacting the analyte with an amplifying agent (and all compounds which are necessary to amplify at least a part of the analyte) and amplifying at least a part of the analyte. Typically only a limited region of the analyte is amplified and in the case of a nucleic acid sequence only the sequence flanked by the two primers will be amplified. The amount of amplification product will then be determined as a function of reaction time, and the first, second or n th order derivative of said function will be calculated, wherein n is a natural number. The maximum, zero value or minimum of said derivative will then be determined and the initial concentration of the analyte will be calculated from said maximum, zero value or minimum. In one preferred embodiment the amplification product is detected by means of fluorescence and the amplification product is obtained by a polymerase chain reaction.

In the context of this invention, the determination of amount of amplification product as a function of time, does not mean, that the absolute amount of amplification product needs to be measured. Instead, it is sufficient to determine relative signals, since relative determination already allows for the calculation of derivatives, which according to the invention may then be used to determine the absolute amount of the initial target concentration.

In one embodiment of the invention the amplification of the analyte is obtained by a polymerase chain reaction and the analyte to be quantified is a nucleic acid. In one accordance with the present invention, the amplification product is typically detected by means of fluorescence. When the analyte is a nucleic acid, the amplification product may be detected by a double-stranded DNA binding entity, for example using a double-strand DNA binding fluorescent dye. Alternatively, the amplification product may be detected with specially designed polynucleotide hybridization probes, which have sequences identical with or complementary to the sequence of the analyte to be quantified over a range of at least 10 contiguous residues. In a specific embodiment of this alternative, two polynucleotide probes are each labeled with a fluorescent entity, such that when both probes are hybridized to the amplification product, Fluorescence Resonance Energy Transfer (FRET) can take place between the two fluorescent entities.

In another aspect of the invention, the signal indicating an interaction between analyte and detecting moiety may also be generated exponentially by using a signal enhancing cascade. Therefore, it is also an aspect of the invention to perform a method for quantification of an analyte comprising a) contacting said analyte with a signal generating binding entity under conditions where a complex between said analyte and said binding entity is formed, b) determining the amount of complex as a function of time, c) calculating the first, second, or n th order derivative of said function, wherein n is a natural number, d) determining the maximum, zero value, or minimum of said derivative, and e) calculating from said maximum, zero value, or minimum the initial concentration of the analyte.

In yet another aspect of the invention, the principle of calculating derivatives in order to generate quantitative data can be applied to the analysis of growth rates of microorganisms or cell populations (see Example 3). Accordingly, the present invention is also directed to a method for analyzing the effect of a compound on the growth rate of a microorganism or a cell population, comprising a) growing said microorganism or cell population in presence of the compound, b) determining the cell number of said microorganism or cell population as a function of growth time, c) calculating the first, second, or n th order derivative of said function, wherein n is a natural number, and d) determining the maximum, zero value or minimum of said derivative as a measure of the effect of said compound.

Also for these embodiments, it is sufficient to determine relative signals reflecting the cell number or amount of complex formation, as long as derivatives may be calculated.

Exponential or progressive amplification of systems may be limited by the availability of some compounds, which can only be provided in limited concentrations. As a consequence, the rate of amplification or self replication starts to decrease and a transition from the exponential phase to a plateau phase takes place, wherein no amplification or self replication product is generated anymore. A typical example for this type of kinetics is amplification of DNA by PCR. In this case, the reaction may be limited by the amount of DNA polymerase, the concentration of amplification primers or the concentration of nucleoside triphosphates. Alternatively, progressive amplification may also be limited by product inhibition; e.g. in the case of PCR by reannealing of single stranded PCR products to form double stranded products that cannot hybridize to the primers.

According to the new invention, a data driven algorithm is used to select data for further analysis. In order to obtain appropriately smoothed kinetics, a mathematic filter algorithm can be used. In case of nucleic acid amplification, preferably, a Savitzky Golay filter may be applied (Numerical Recipes in C, the art of scientific Computing, Cambridge University Press, second edition, p. 650 ff).

Upon applying a Savitzky Golay filter, each measured kinetic point is replaced by a smoothened point, calculated from a window including points to the left and to the right of the neighborhood. From these points, a polynomial of n th order is calculated for every measured value, with the exception of those values determined at the very beginning and the very end of the reaction, where due to lack of points to the left or to the right, such a calculation is impossible. Accordingly, vertical window parameters are defined as a/n/b, wherein a is the number of points taken from the left, n is the order of the polynomial and b is the number of points taken from the right.

From the smoothened kinetic values, the maximum, minimum or zero value of the first, second or n th derivative is calculated. Determination of such extrema provides suitable set points for the definition of an unique and reliable fractional cycle number characteristic for each kinetic value, which reflects the initial concentration of the analyte.

It has been proven to be particularly advantageous to use a Savitzky Golay filter having the vertical window parameters 3/3/4 in combination with the calculated maximum of the first derivative, or, alternatively, a Savitzky Golay filter with the vertical window parameters 6/2/4 in combination with the calculated maximum of the second derivative in order to obtain the most reliable data.

For each smoothened kinetic point, derivatives are calculated by methods known in the art. For example the first derivative for each smoothened value y for a given cycle number x of a polymerase chain reaction may be calculated as $f'(x)=y(x)-y(x-1)$. The second derivative can then be calculated from the first derivative in the same manner. Alternatively, at a given cycle x the polynomial fit from the Savitzky Golay filter can be easily evaluated for first and second derivatives of y and x.

Figure 4:
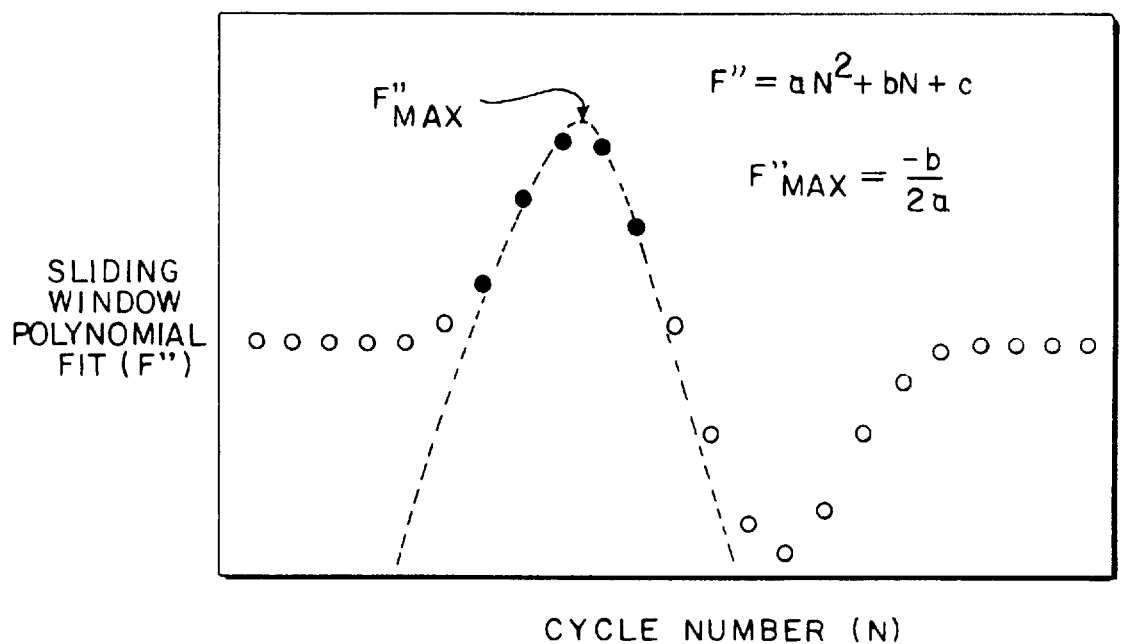

Subsequently, in order to determine the extrema from said derivatives, a further polynomial fit may be applied, for which a number of three to five points are taken into account, which are located around the presumed extremum. For example FIG. 4 shows the fractional cycle number determination of the second derivative maximum using a quadratic fit to five points. The second derivative values were determined by a sliding window polynomial fit (a Savitzky Golay filter).

The possibility of measuring the kinetics of an amplification reaction, which is a prerequisite for the new invention, has become enormously facilitated since there are instruments and methods available, wherein the generation of the amplification product can be measured continuously by spectroscopic detection principles, for example by means of fluorescence. An example for a suitable instrument is described in detail in Wittwer et al., Biotechniques 22, No. 1, 176–181 (1997).

Several detection formats based on target dependent fluorescent signaling have been disclosed, which enable continuous monitoring of the generation of amplification products (reviewed in Wittwer et al., Biotechniques, Vol. 22, No, 1, 130–138, (1997)). These detection formats include but are not limited to:

1. Use of Fluorescent Double-stranded DNA Recognizing Compounds

Since the amount of double stranded amplification product usually exceeds the amount of nucleic acid originally present in the sample to be analyzed, double-stranded DNA specific dyes may be used, which upon excitation with an appropriate wavelength show enhanced fluorescence only if they are bound to double-stranded DNA. Preferably, only those dyes may be used which like SYBR Green I, for example, do not affect the efficiency of the PCR reaction.

2. Increased Fluorescence Resonance Energy Transfer upon Hybridization

For this detection format, two oligonucleotide hybridization probes each labeled with a fluorescent moiety are used which are capable of hybridizing to adjacent but non-overlapping regions of one strand of the amplification product. Preferably, one oligonucleotide is labeled at the 5' end and the second oligonucleotide is labeled at the 3' end. When hybridized to the target DNA, the two fluorescent labels are brought into close contact, such that fluorescence resonance energy transfer between the two fluorescent moieties can take place. As a consequence, the hybridization can be monitored through excitation of the donor moiety and subsequent measurement of fluorescence emission of the second acceptor moiety.

In a similar embodiment, only one fluorescently labeled probe is used, which together with one appropriately labeled primer may also serve as a specific FRET pair (Bernard et al., Analytical Biochemistry 235, p. 101–107 (1998)).

3. Tag Man Principle

In order to detect the amplification product, a single-stranded hybridization probe is used, which is labeled with a fluorescent entity, the fluorescence emission of which is quenched by a second label on the same probe which may act as a quenching compound. During the annealing step of the PCR reaction, the probe hybridizes to its target sequence, and, subsequently, during the extension of the primer, the DNA polymerase having a 5'-3'-exonuclease activity digests the hybridization probe into smaller pieces, such that the fluorescent entity is separated from the quencher compound. After appropriate excitation, fluorescence emission can be monitored as an indicator of accumulating amplification product.

4. Molecular Beacons

Similar to the Taq Man Probes, a molecular beacon oligonucleotide is labeled with a fluorescent compound and a quencher compound, which due to the secondary structure of the molecule are in close vicinity to each other. Upon binding to the target DNA, the intramolecular hydrogen bonding is broken, and the fluorescent compound located at one end of the probe is separated from the quencher compound, which is located at the opposite end of the probe (Lizardi et al., US 5, 118, 801).

Usually, the hybridization probes as disclosed have sequences which are completely identical with or exactly complementary to the sequence of the analyte. However, it is also within the scope of the invention, if the probes contain one or several mismatches, as long as they are capable of hybridizing to the analyte under appropriate hybridization conditions. In any case, it has been proven to be particularly advantageous, if the sequence identity or complementary is 100% over a range of at least 10 contiguous residues. It has also been proven to be advantageous, if the length of the probe does not exceed 100 nucleotides, preferably not more than 40 nucleotides.

In the case of quantification of an analyte according to the principle of using external standards, a calibration curve has to be generated. When the analyte to be quantified is a nucleic acid which is amplified by PCR, known amounts of the analyte are amplified and the intensity of fluorescent signal is determined as a function of cycle number. After smoothening of the kinetics by a mathematical fit, one or more extrema of the first, second or n th derivative are calculated. This enables a correlation between the original target concentration and the fractional cycle number of a determined extremum. Subsequently, determination of unknown analyte concentrations may be performed.

EXAMPLE 1

Amplification of a CyclophillinA sequence by PCR and subsequent detection with HybProbes: Comparison with a previously disclosed algorithm A linearized plasmid carrying the CyclophillinA sequence was subjected to serial dilutions to produce concentrations of $10^7$, $10^5$, $10^3$, and $10^2$ copies per 2 μl. In order to obtain reliable statistical data, these dilutions were prepared in 6 fold replicates. In a total volume of 20 μl, for each sample a PCR reaction was set up:

1 × LCDNA Master mix hybridization probes
(Roche Mol. biochem. Catalogue No. 2015102)
4 mM $MgCl_2$
1 μM CycA1 forward primer (pos. 52–69)
1 μM CycA2 reverse primer (pos. 471–493)
200 nM 3' Fluorescein CycA hybridization probe (pos. 420–439)
200 nM 5' LC RED640 CycA hybridization probe (pos. 444–470)
$10^7$, $10^5$, $10^3$, and $10^2$ copies of CycA plasmid.

Nucleotide positions of primers and probes as indicated correspond to nucleotide positions as given in Haendler et al. (Embo Journal 6, p. 947–950 (1987)).

According to the manufacturer's protocol, the samples were filled in 1.5 mm capillaries (Roche Mol. Biochem. Cat. No. 1909 339). Subsequently, the capillaries were inserted into a Roche Diagnostics GmbH LightCycler LC 32 and subjected to a PCR reaction according to the following thermocycling protocol:

| | Temp. (° C.) | Time (sec) | Ramp rate (° C./s) | Acqu. | Cycles |
|---|---|---|---|---|---|
| Denaturation | 95 | 120 | 20.0 | None | X 1 |
| Denaturation | 95 | 0 | 20.0 | None | X 45 |
| Annealing | 55 | 10 | 10.0 | Single | X 45 |
| Elongation | 72 | 15 | 3.0 | None | X 45 |

After each cycle, according to the manufacturer's protocol, fluorescence was analyzed for each sample in two different channels, wherein channel 1 corresponded to a bypass of 520+/−20 nm and channel 2 corresponded to a bypass of 645+/−20 nm. Subsequently, the ratio of the values obtained from channel 2 versus channel 1 was calculated in order to normalize volume differences due to pipetting errors and exclude alignment and detection errors.

Figure 1B:
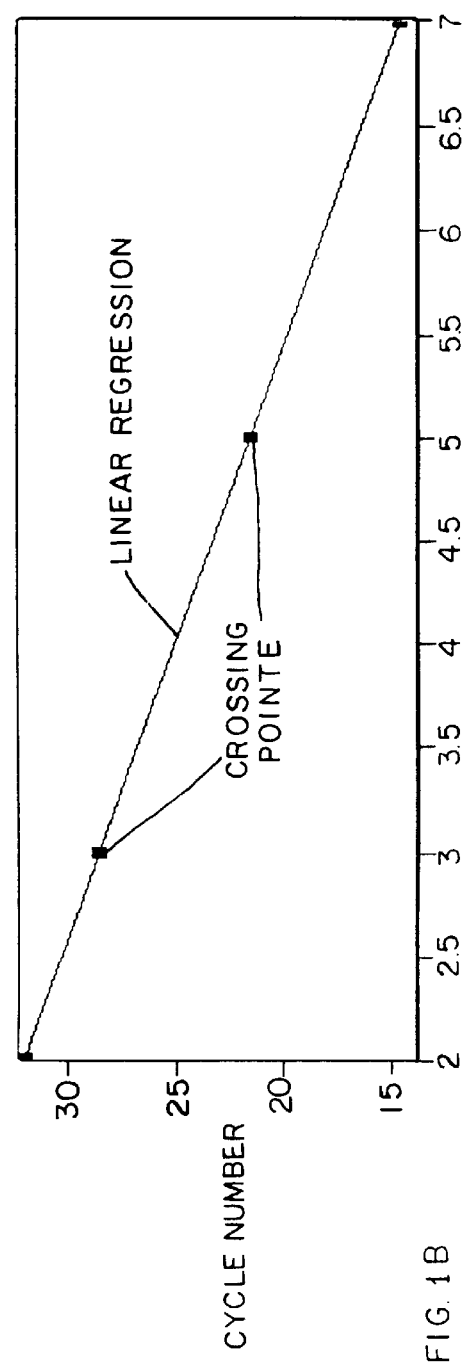
FIG. 1B: Linear regression curve calculated with the threshold method according to Example 1.

Raw data obtained in Example 1 were processed in two different ways:

A) According to the previously disclosed method, a manually chosen threshold level was set after appropriate background subtraction of raw fluorescent data. For each sample, the intersection between the threshold line and the function of fluorescent signal versus time was calculated with the following algorithm: Based on a regression calculation, two measured points above a previously defined noise band were used to define a log linear phase by means of linear regression. Within the log linear area, a threshold line was set manually, and the intersection between the threshold line and the regression lines corresponding to each tested copy number were calculated. In order to gain information on the validity of the method, the calculated crossing points were used to create a plot indicating cycle number versus calculated log 1O of initial concentrations of the target DNA (see FIGS. 1A and 1B). From this plot, a linear regression was determined, which enabled the calculation of mean values, standard deviations and variation coefficients as indicators for the accuracy and precision of the method. Results are shown in Table 1, wherein concentrations and crossing points were calculated with the fluorescence threshold method according to Example 1, and the abbreviations are as follows: mean values (Mittelwert) standard deviations (STDWN) and variation coefficients (CV (%)).

TABLE 1

| experiment | copy No. | calculated conc. | | | | | | Mittelwert | STDWN | CV (%) |
|---|---|---|---|---|---|---|---|---|---|---|
| 280998#84 | 1.00E+07 | 10,020,000 | 10,030,000 | 10,670,000 | 10,290,000 | 8,984,000 | 9,630,000 | 9937333.33 | 529133.464 | 5.32420277 |
| cycA-1 | 1.00E+05 | 105,800 | 106,900 | 105,300 | 103,000 | 95,790 | 91,780 | 101428.333 | 5647.08579 | 5.56835117 |
| | 1.00E+03 | 1,039 | 1,024 | 1,032 | 1,003 | 929.3 | 980.4 | 1001.28333 | 37.6447613 | 3.75965125 |
| | 1.00E+02 | 106.5 | 96.39 | 93.71 | 92.89 | 111.1 | 97.57 | 99.6933333 | 675708188 | 6.77786734 |

| experiment | copy No. | crossing points | | | | | | Mittelwert | STDWN | CV (%) |
|---|---|---|---|---|---|---|---|---|---|---|
| 280998#84 | 1.00E+07 | 14.49 | 14.48 | 14.39 | 14.45 | 14.65 | 14.55 | 14.5016667 | 0.08173467 | 0.56362256 |
| cycA-1 | 1.00E+05 | 21.34 | 21.33 | 21.35 | 21.38 | 21.49 | 21.56 | 21.4083333 | 0.08629729 | 0.40310139 |
| | 1.00E+03 | 28.31 | 28.33 | 28.32 | 28.36 | 28.47 | 28.39 | 28.3633333 | 0.05467073 | 0.19275143 |
| | 1.00E+02 | 31.74 | 31.89 | 31.93 | 31.94 | 31.67 | 31.87 | 31.84 | 0.10033278 | 0.31511551 | analysis: Fit Points; proportional

Figure 2A:
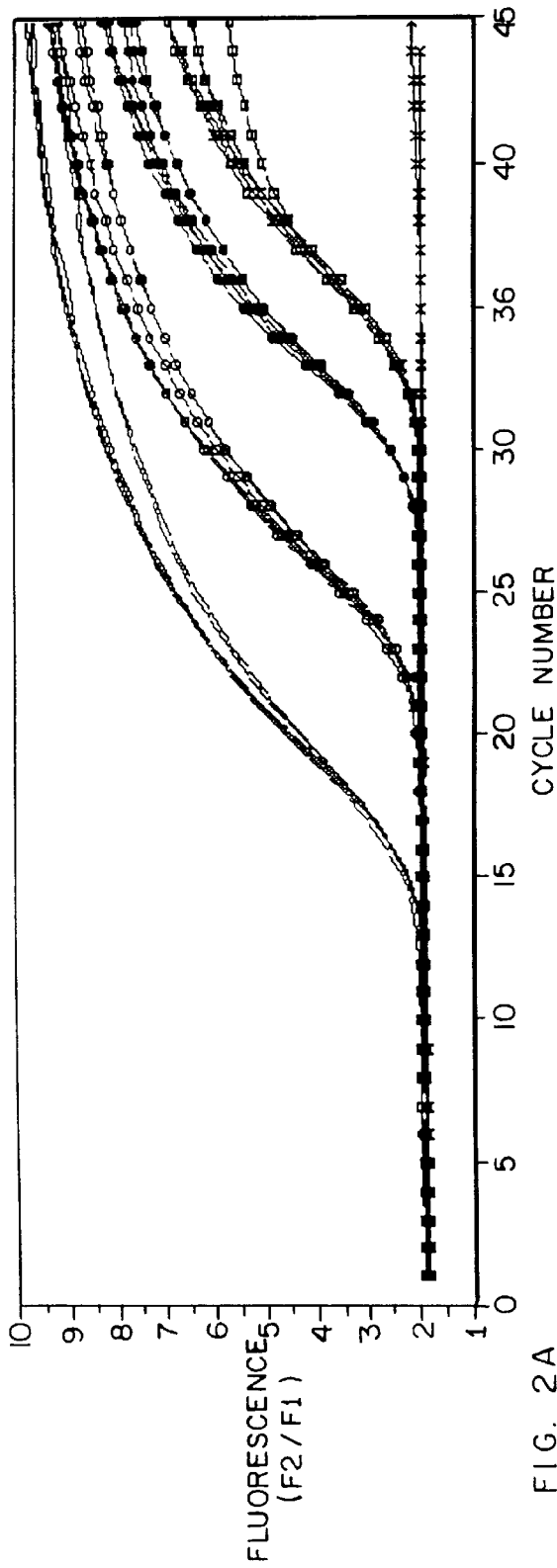
FIG. 2A: Measurement of fluorescence signal with FRET-HybProbes.
Figure 2B:
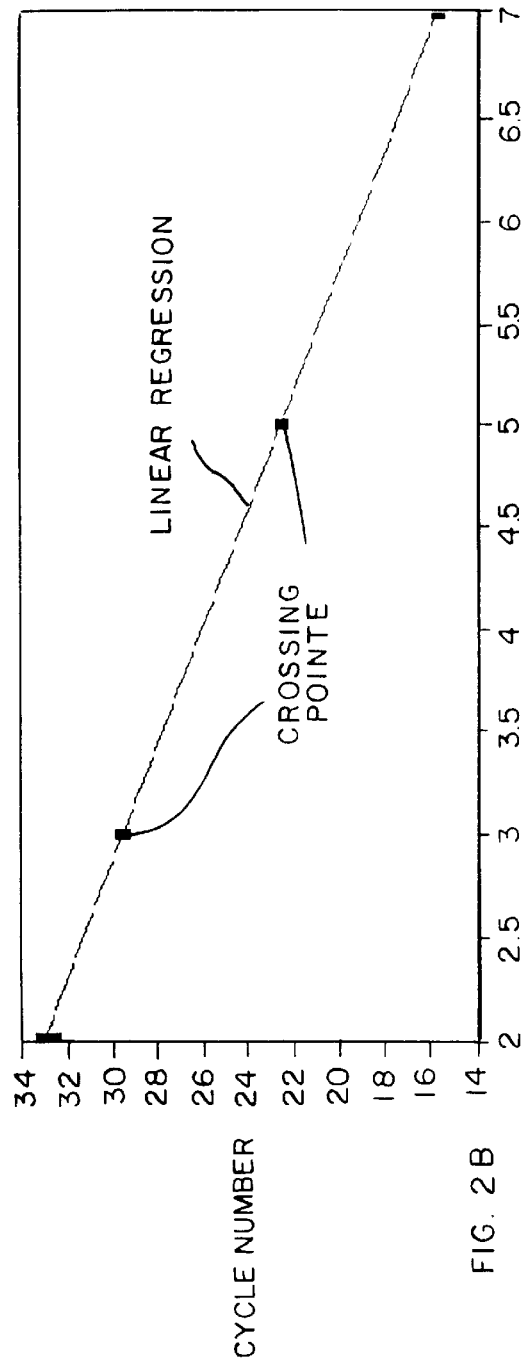
FIG. 2B: Linear regression curve calculated with the second derivative maximum method according to Example 1.
Figure 3A:
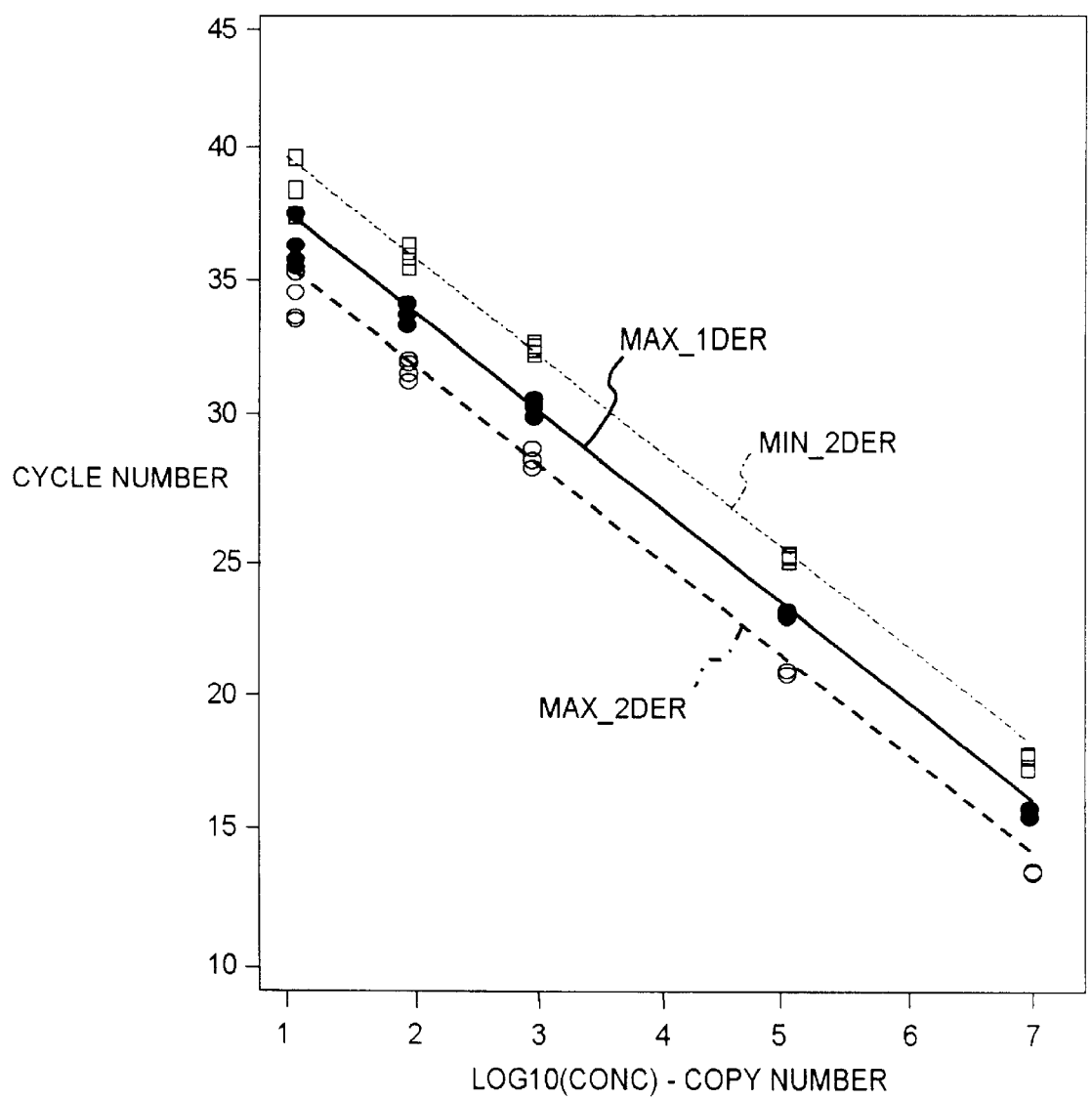
FIGS. 3A–3J: Plots showing fractional cycle numbers as calculated in six fold replicate by determining the maximum first derivative, minimum second derivative, and maximum second derivative versus log 10 of template copy number in a SYBR Green experiment according to Example 2. Savitzky Golay filter vertical window parameters were set as follows FIG. 3A, 2/3/2.
Figure 3B:
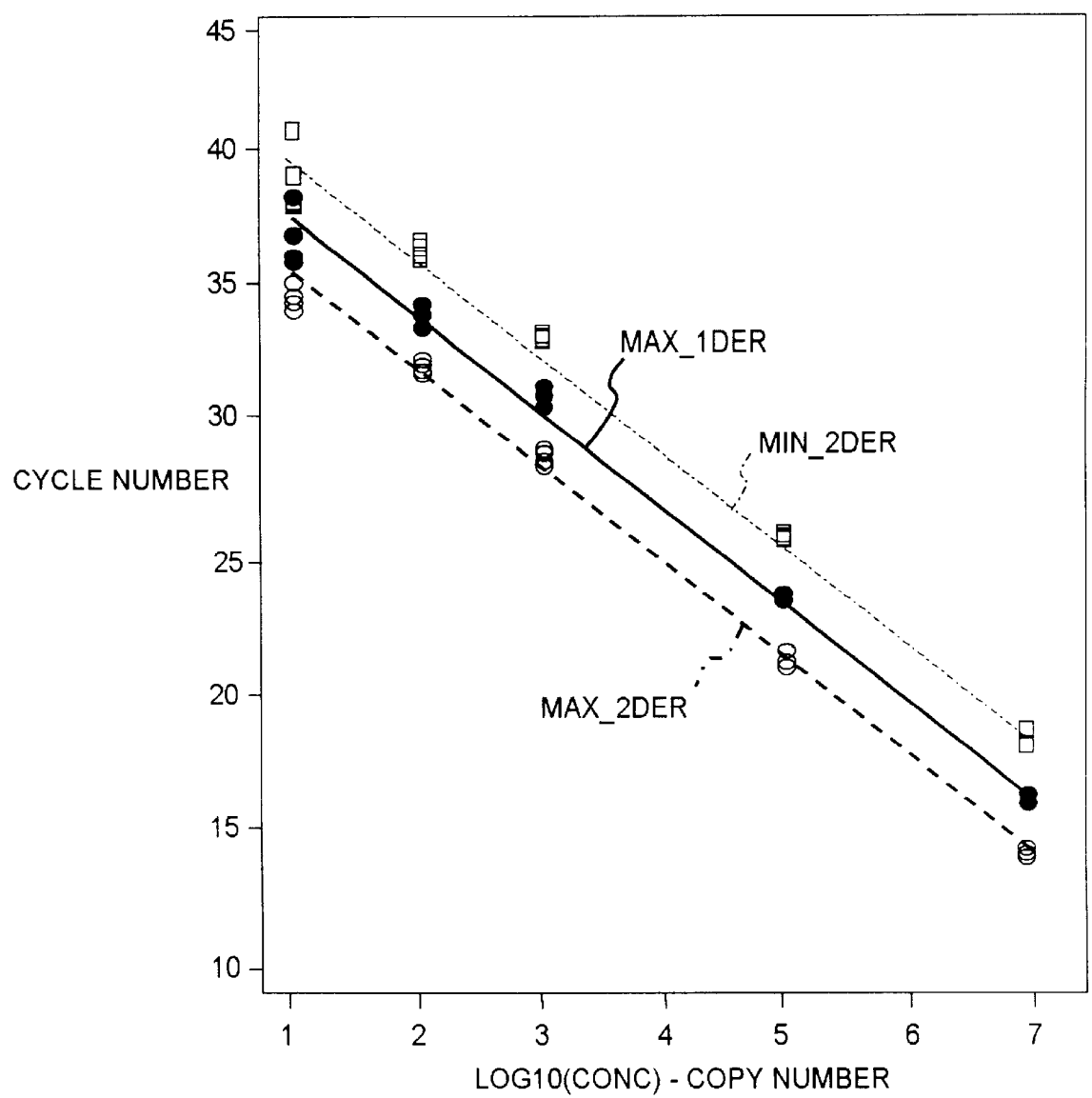
Figure 3C:
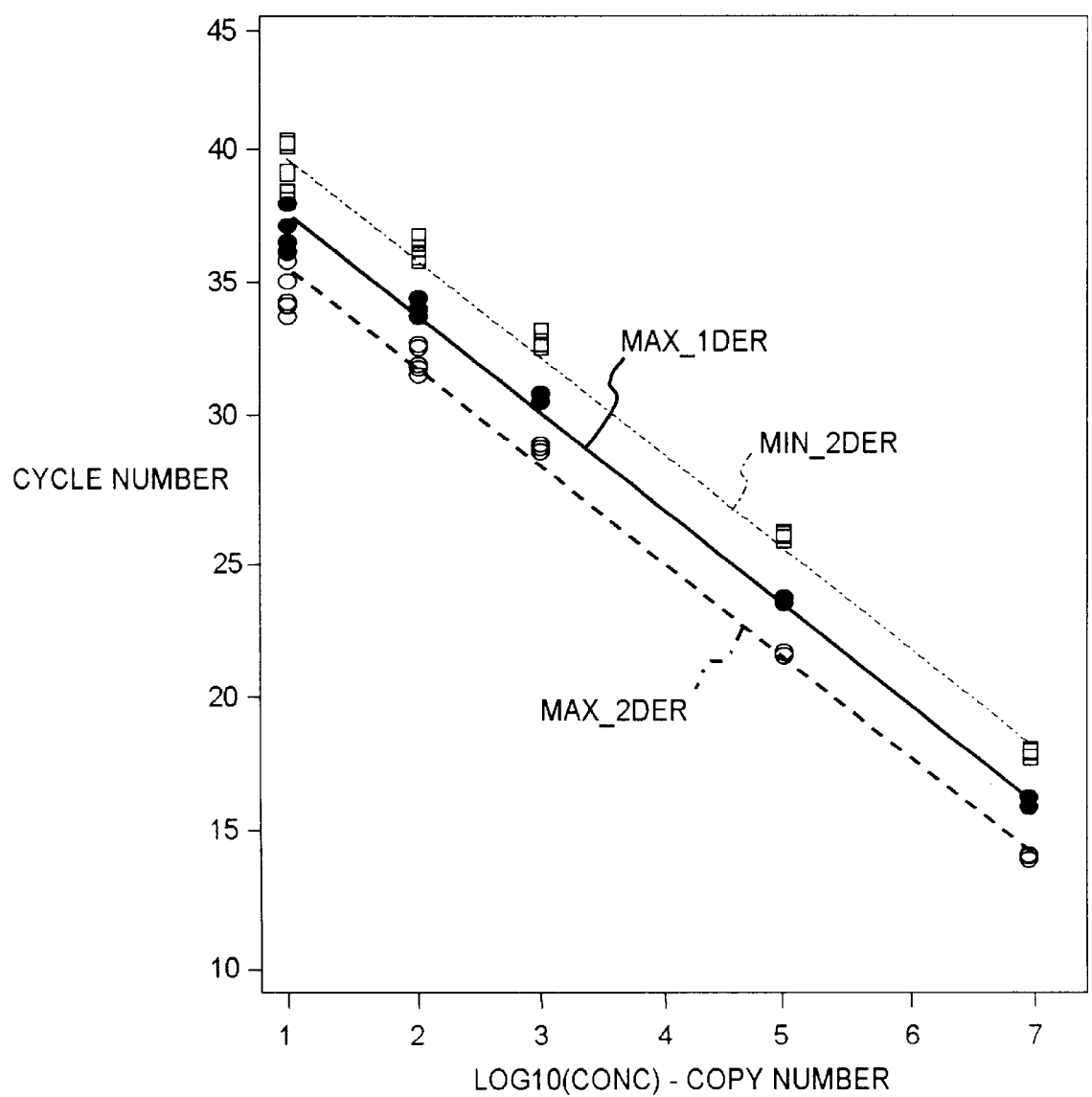
Figure 3D:
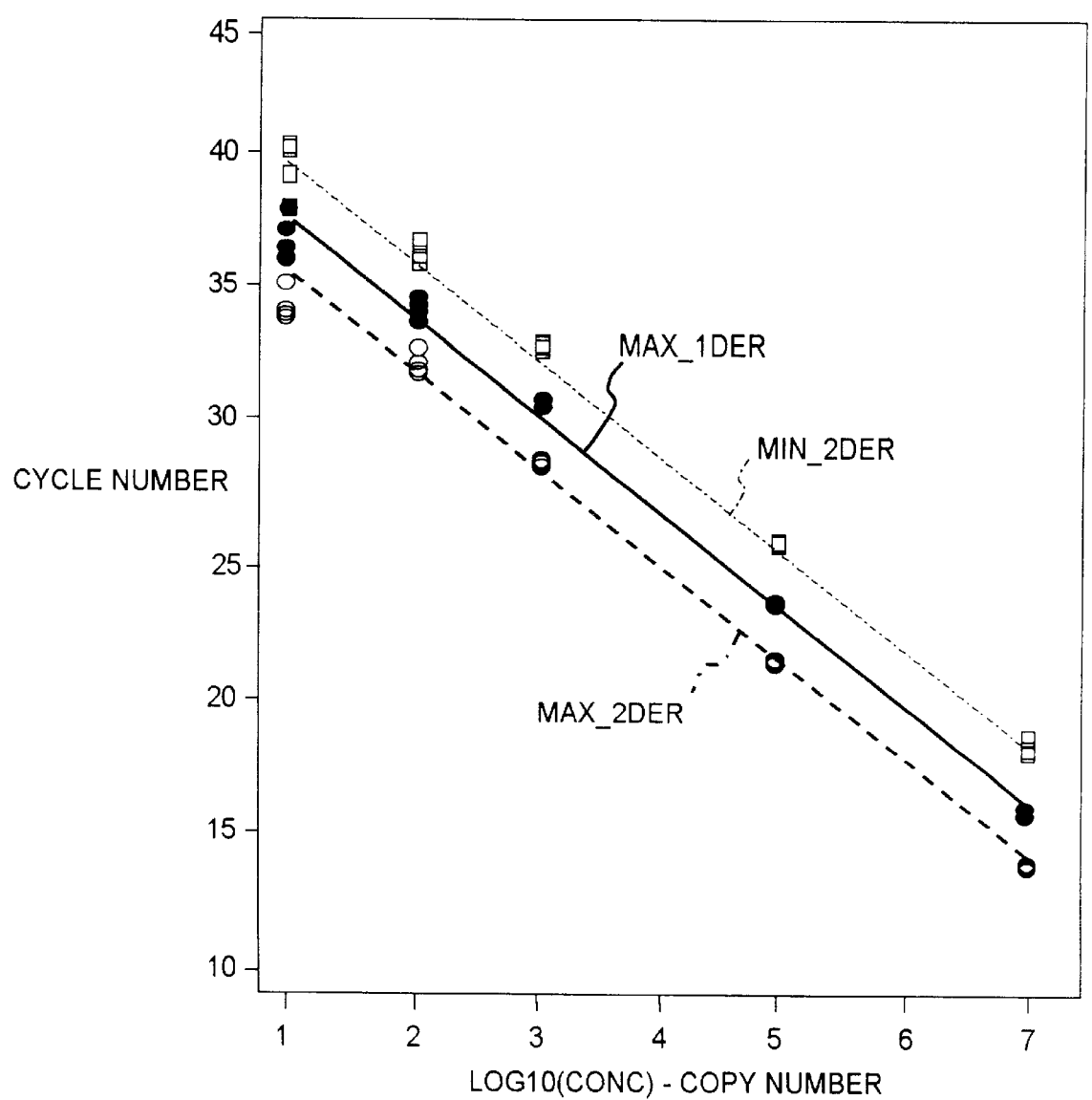
Figure 3E:
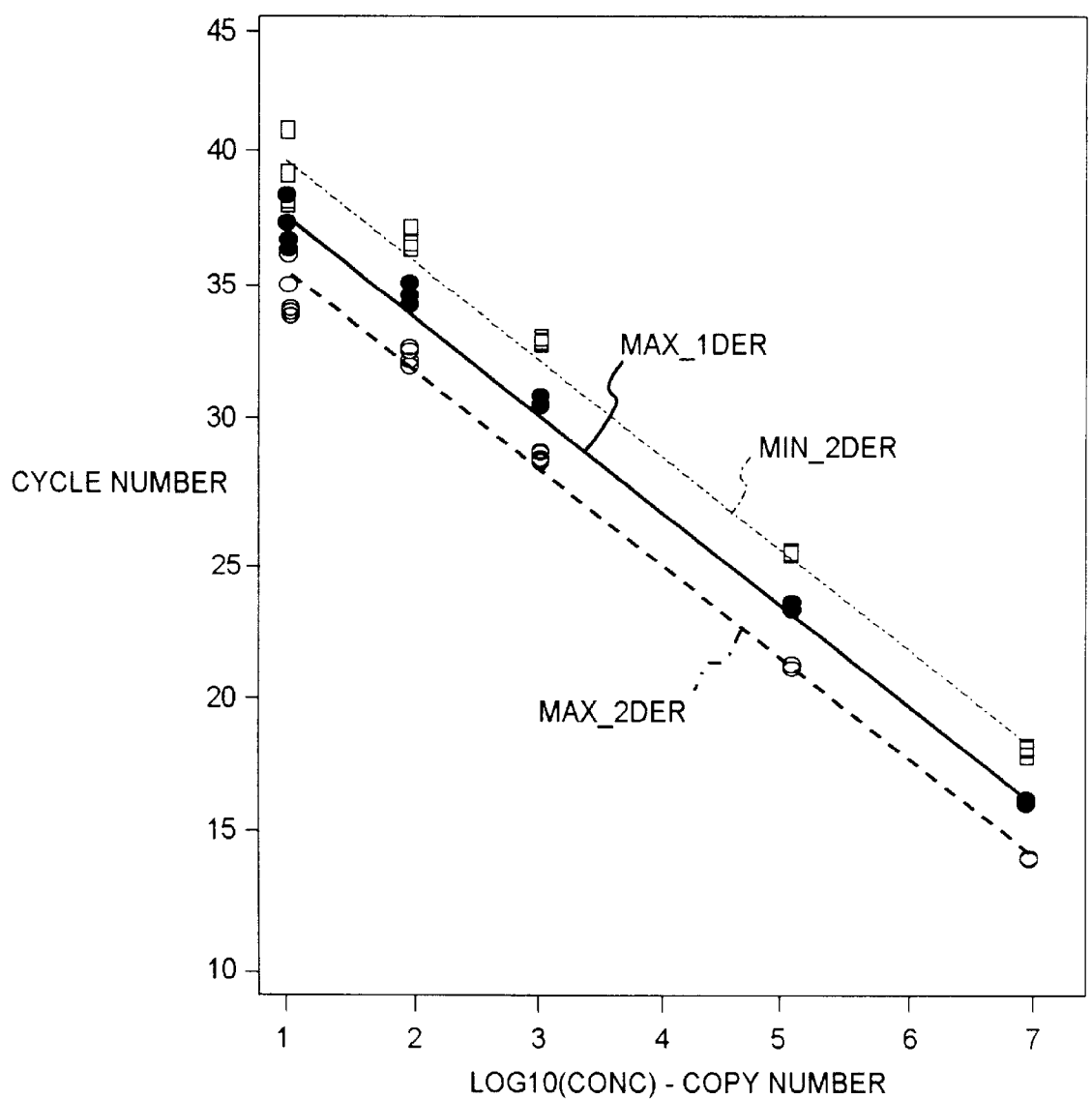
Figure 3F:
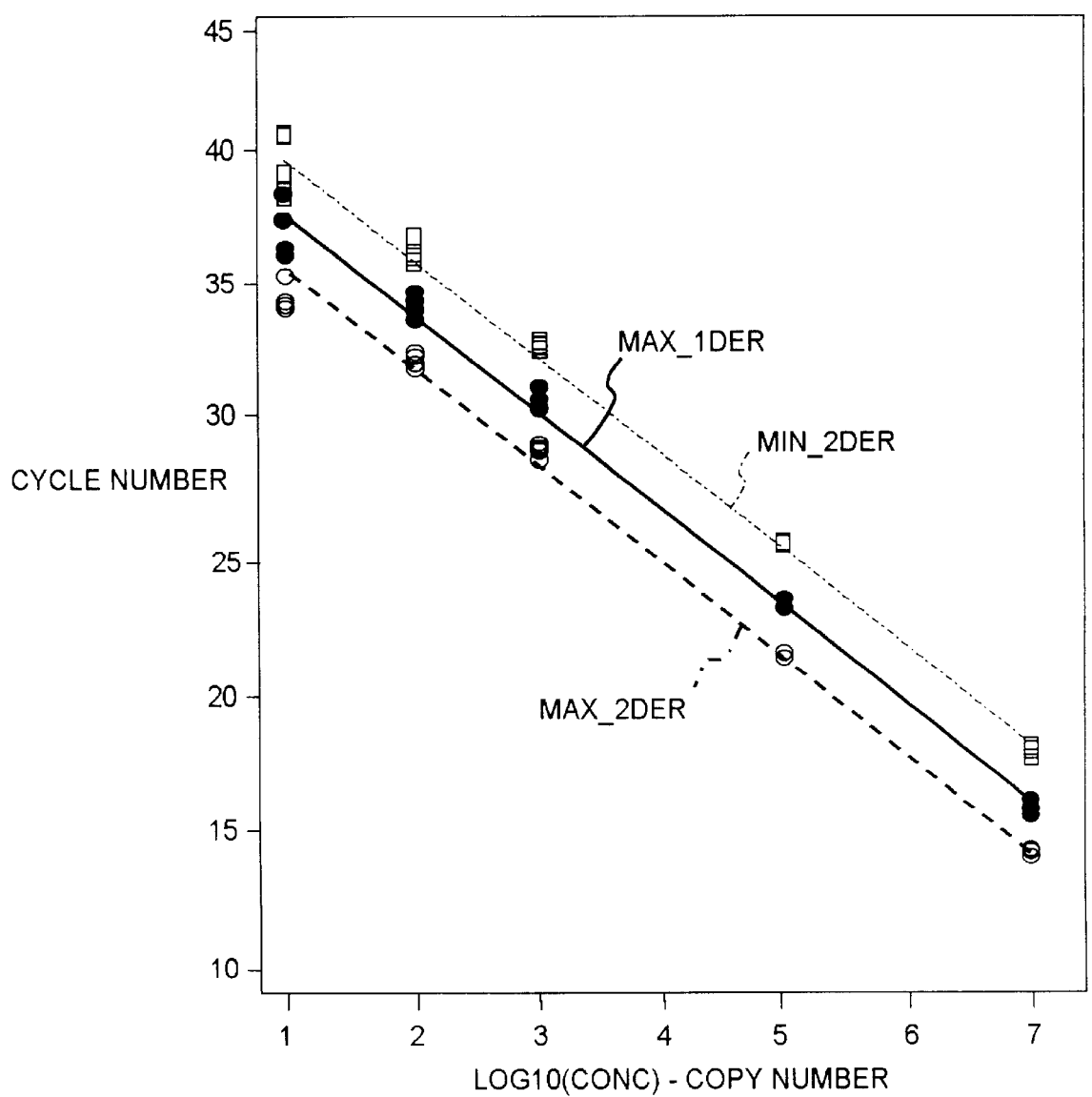
Figure 3G:
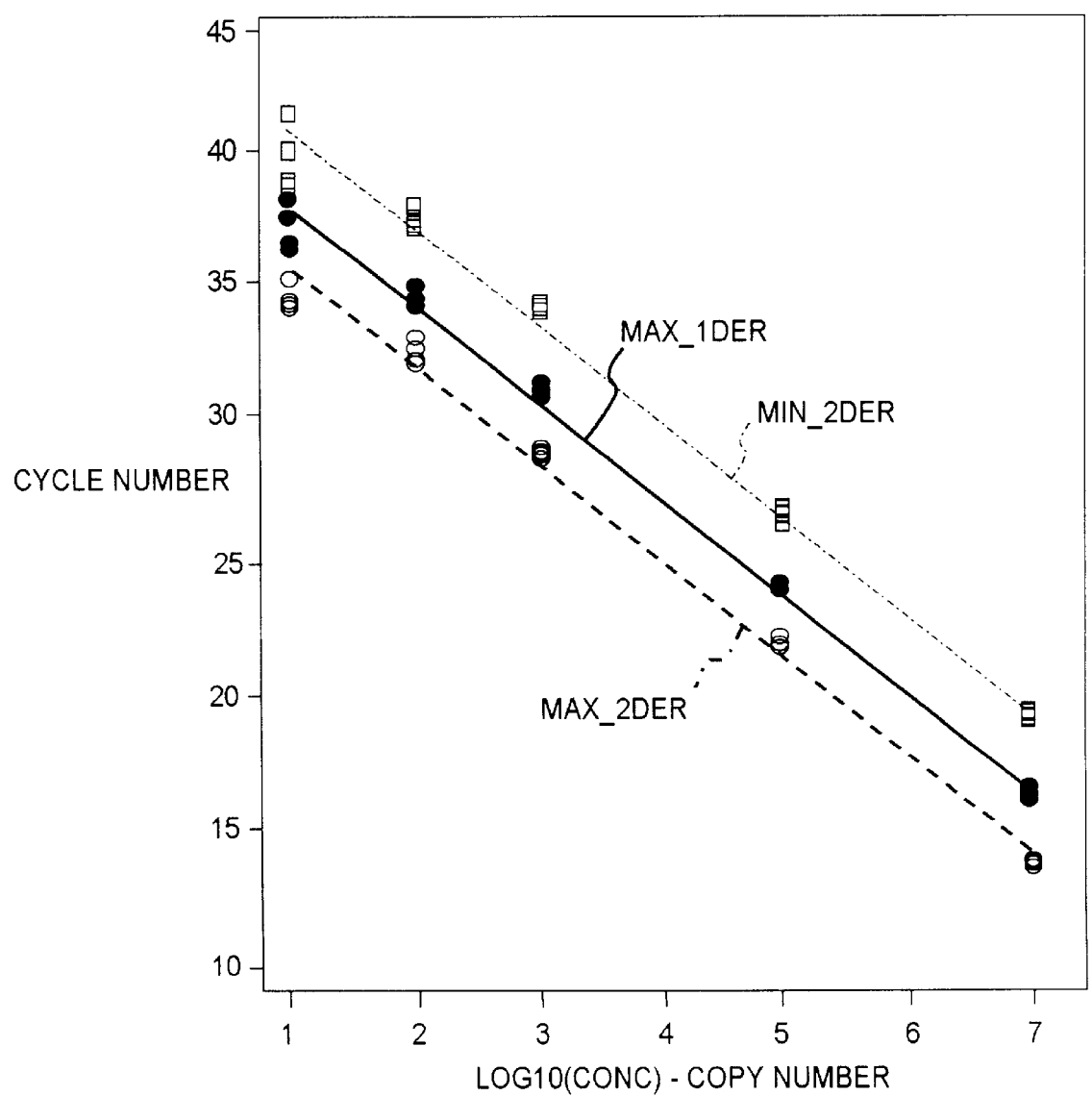
Figure 3H:
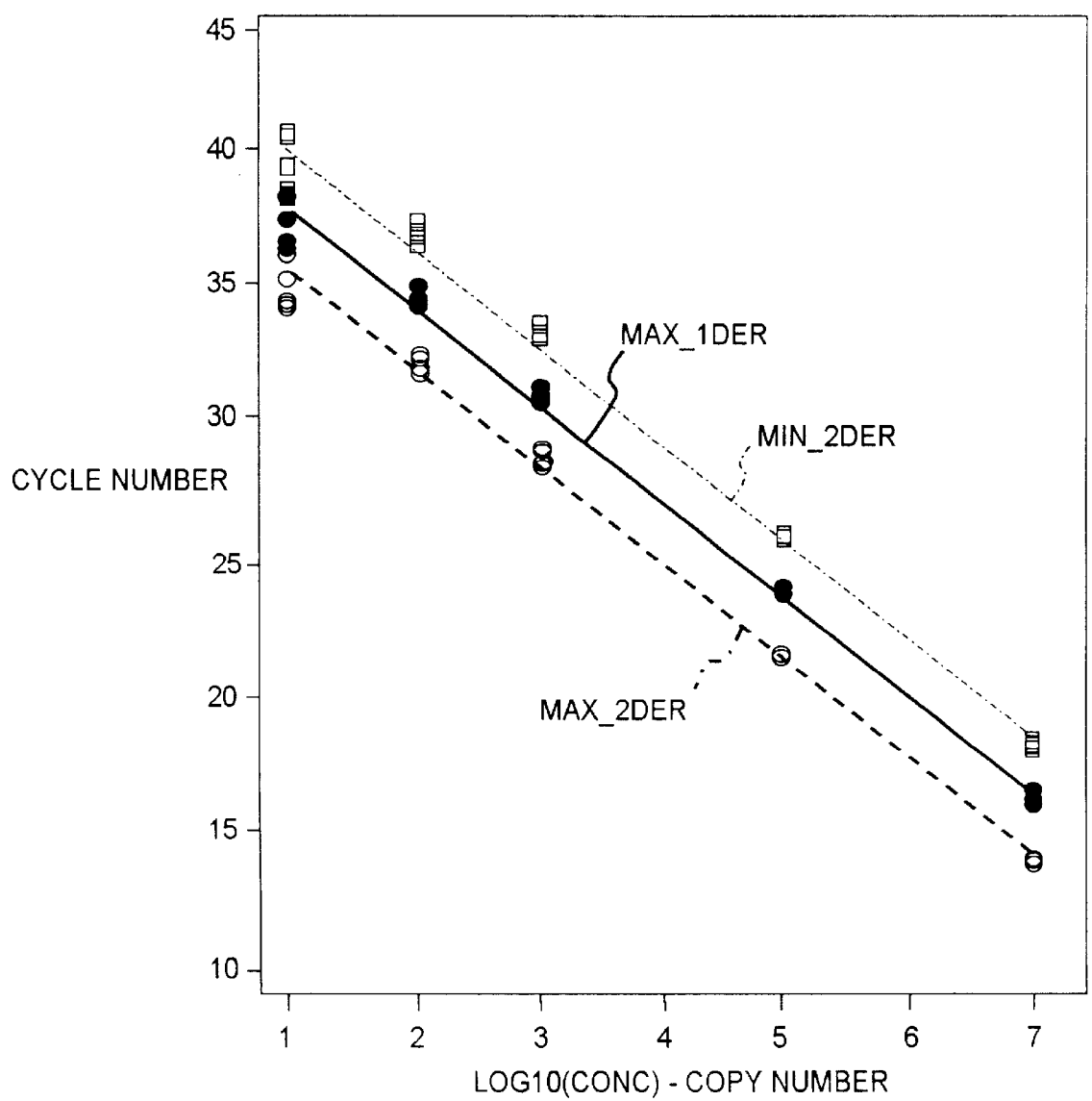
Figure 3I:
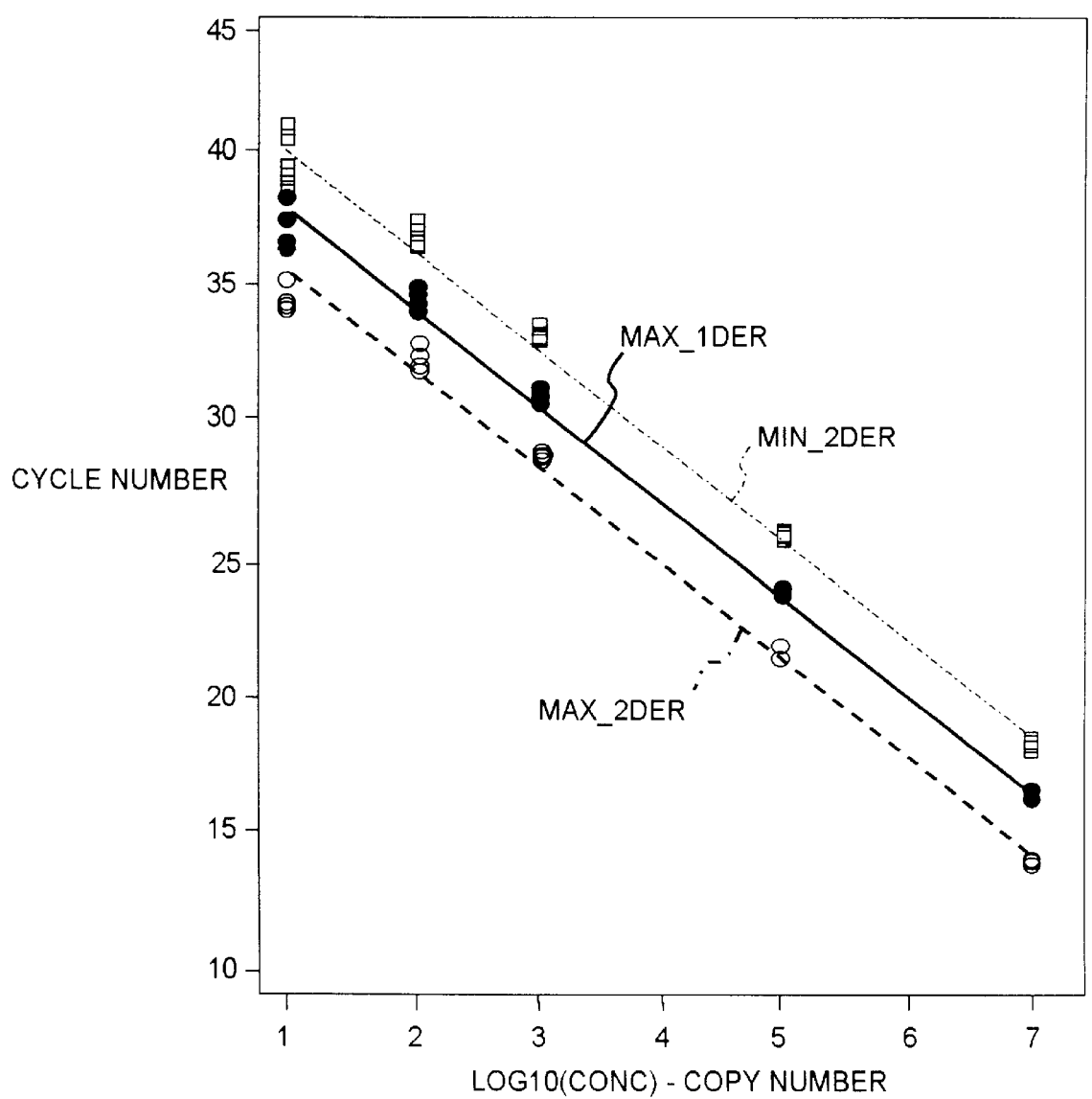
Figure 3J:
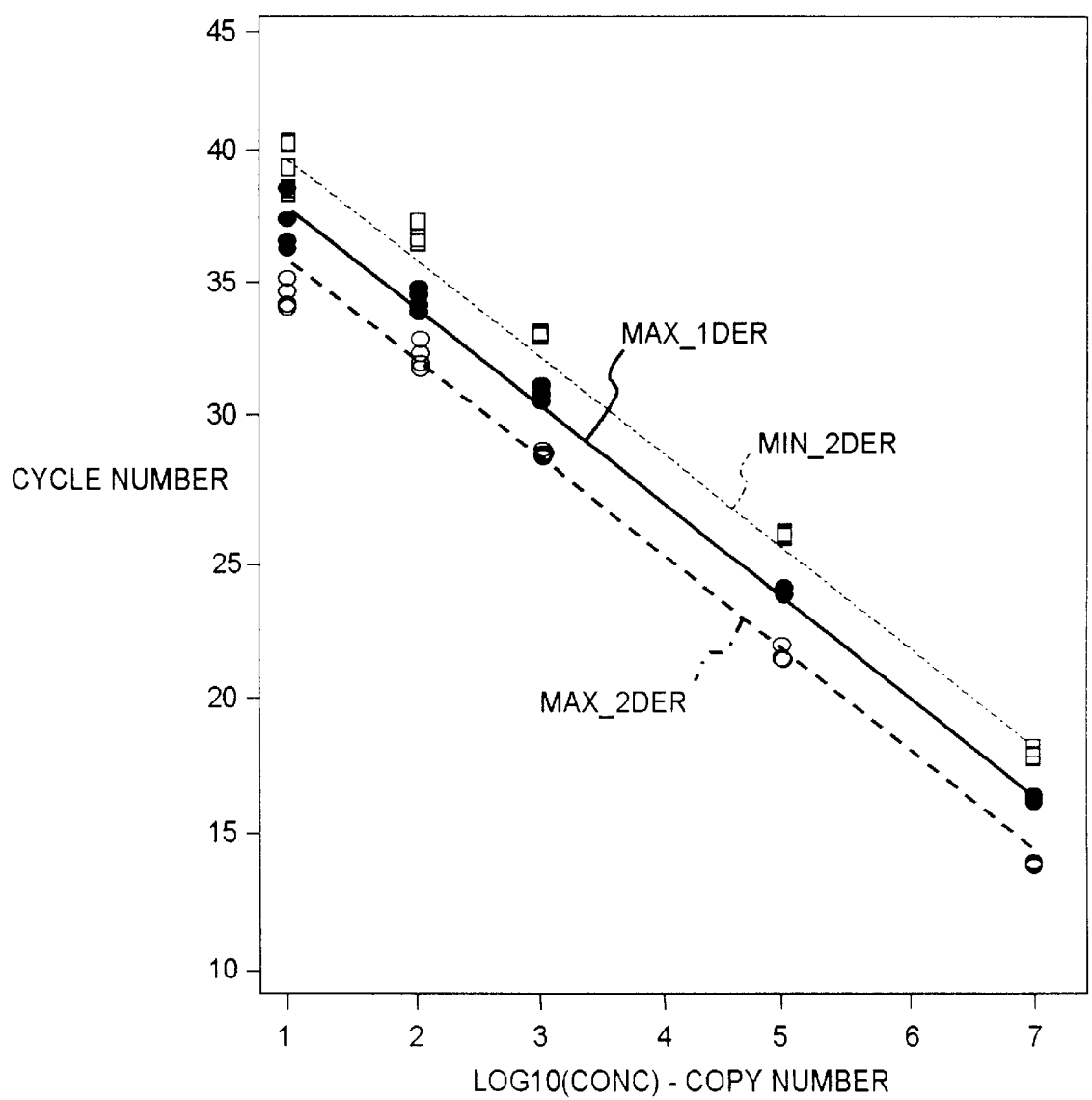

B) According to the new invention, the same raw data were smoothened by a polynomial fit using a Savitzky Golay Filter having the vertical window parameters 6/2/4 without previous background subtraction. From the obtained function, the maximum of the second derivative was calculated and used as an indicator for the initial template concentration. Again, from the obtained data, a plot indicating the fractional cycle number versus initial concentrations of target DNA was created (see Figs. 2A and 2B). Mean values, standard deviations and variation coefficients were calculated as described above, results of which are shown in Table 2 wherein concentrations and crossing points were calculated with the second derivative maximum method according to Example 1, and the abbreviations are as follows: mean values (Mittelwert) standard deviations (STDWN) and variation coefficients (CV(%)).

As can be seen by comparison of results from Tables 1 and 2, the statistic values either obtained by method A) according to prior art, or obtained by method B) according to the invention yielded about the same degree of accuracy and precision. However, since the method according to the new invention is independent from the actual amount of generated fluorescent signal and data processing is not user driven, it provides a superior advantage over the previously disclosed quantification methods.

maximum, the second derivative maximum and the second derivative minimum.

The experiment was carried out according to Example 1 with the following modifications:

A plasmid carrying a TNF-alpha genomic sequence (Shirai et al., Nature 313, p 803, (1985)) was subjected to serial dilutions to produce sample concentrations of $10^7$, $10^5$, $10^3$, $10^2$ and $10^1$ copies per 2 µl. 6 fold replicates were prepared for each sample concentration.

In a total volume of 20 µl, each PCR reaction contained:

---

1 × LCDNA Master mix SYBR GreenI
(Roche Mol. biochem. Catalogue No. 2015099)
3 mM $MgCl_2$
1 µM TNF-alpha forward primer (Roche Mol. Biochem. Cat. No. 1 989 626)
1 µM TMF-alpha reverse primer (Roche Mol. Biochem. Cat. No. 1 989 626)
$10^7$, $10^5$, $10^3$, $10^2$ and $10^1$ copies of TNF-alpha cDNA containing plasmid.

---

The applied thermocycling protocol was identical to Example 1. After each cycle of amplification, SYBR Green fluorescence was measured according to the manufacturers' protocol in LightCycler channel 1, corresponding to a bypass of 520+/−20 nm.

According to the new invention, the raw data were smoothened by different polynomal fits using a Savitzky

TABLE 2

| experiment | copy No. | calculated conc. | | | | | | Mittelwert | STDWN | CV (%) |
|---|---|---|---|---|---|---|---|---|---|---|
| 280998#84 | 1.00E+07 | 9,555,000 | 10,450,000 | 10,870,000 | 10,790,000 | 9,438,000 | 9,914,000 | 10169500 | 567506.755 | 5.58047844 |
| cycA-1 | 1.00E+05 | 91,000 | 99,240 | 100,900 | 99,170 | 105,100 | 98,410 | 98970 | 4188 26137 | 4.23184942 |
| | 1.00E+03 | 933.3 | 904.2 | 993 | 903.2 | 929.1 | 1,101 | 960.633333 | 69.4924137 | 7.23402064 |
| | 1.00E+02 | 102.9 | 84.07 | 88.19 | 100.9 | 138 | 118.6 | 105.443333 | 18.3241268 | 17.3781748 |

| experiment | copy No. | crossing points | | | | | | Mittelwert | STDWN | CV (%) |
|---|---|---|---|---|---|---|---|---|---|---|
| 280998#84 | 1.00E+07 | 15.79 | 15.66 | 15.6 | 15.61 | 15.81 | 15.74 | 15.7016667 | 0.0831498 | 0.52956033 |
| cycA-1 | 1.00E+05 | 22.79 | 22.66 | 22.63 | 22.66 | 22.57 | 22.67 | 22.6633333 | 0.06574361 | 0.290088 |
| | 1.00E+03 | 29.67 | 29.72 | 29.57 | 29.72 | 29.67 | 29.42 | 29.6283333 | 0.10573815 | 0.35688186 |
| | 1.00E+02 | 32.98 | 33.28 | 33.21 | 33.01 | 32.54 | 32.77 | 32.965 | 0.25171081 | 0.76356989 | analysis: second derivative maximum; baseline coorection not relavant for results

EXAMPLE 2

Amplification of a TFN-alpha sequence by PCR and subsequent detection with SYBR Green: Comparison of calculating initial concentrations from the first derivative Golay Filter having the vertical window parameters 2/3/2, 2/4/2, 3/3/3, 3/4/3, 4/3/2, 4/4/2, 6/3/2, 6/4/2, 6/5/2, and 6/6/2. From the obtained kinetics, the maximae of first derivatives, second derivatives and the minimae of second derivatives were calculated for all six replicates of a given analyte concentration and used as an indicator for the initial template concentration.

Based on these data, cycle numbers were plotted against the log 10 of different copy numbers of template DNA. Subsequently, a regression line was calculated. As can be deduced from FIGS. 3A–3J, the results of these calibration performance plots demonstrate the linear relation between the calculated cycle number and the log 10 of analyte concentration, proving that principally determining different extrema by using different types of vertical window parameters may be used for determining initial analyte concentrations.

In order to determine preferable embodiments regarding the selection of appropriate Savitzky-Golay filters with respect to the first and second order maxima, the data from the different plots were compared mainly by taking the following 3 criteria into account:

a) variation coefficient (CV (%)) as determined for the 6 replicates representing 100 copies of in analyte, b) slope of the straight regression line, as an indicator for the separation potential, c) separation potential for discriminations between $10^1$ and $10^2$ copies of analyte, calculated by the robust statistical Wilcoxon Test wherein p values are determined, for which a number of less than 0.05 is regarded as significant.

The results of this analysis are summarized in Table 3.

TABLE 3

| Derivative | Filter-Parameter | Slope | Separation Potential 10<>100 copies | CV % at 100 copies |
|---|---|---|---|---|
| 1st | 2/3/2 | −3.29 | .0042 | 1 |
| 1st | 2/4/2 | −3.33 | .0038 | 1 |
| 1st | 3/3/3 | −3.29 | .0040 | 0.85 |
| 1st | 3/4/3 | −3.29 | .0041 | 0.85 |
| 1st | 4/3/2 | −3.30 | .0040 | 0.76 |
| 1st | 4/4/2 | −3.29 | .0043 | 0.93 |
| 1st | 6/3/2 | −3.29 | .0041 | 0.85 |
| 1st | 6/4/2 | −3.30 | .0037 | 0.81 |
| 1st | 6/5/2 | −3.29 | .0039 | 0.9 |
| 1st | 6/6/2 | −3.31 | .0041 | 0.91 |
| 2nd | 2/3/2 | −3.42 | .0042 | 1.26 |
| 2nd | 2/4/2 | −3.27 | .0036 | 7.69 |
| 2nd | 3/3/3 | −3.37 | .0035 | 0.67 |
| 2nd | 3/4/3 | −3.43 | .0038 | 1.32 |
| 2nd | 4/3/2 | −3.40 | .0037 | 1.18 |
| 2nd | 4/4/2 | −3.41 | .0037 | 1.78 |
| 2nd | 6/3/2 | −3.39 | .0043 | 0.96 |
| 2nd | 6/4/2 | −3.39 | .0044 | 1.09 |
| 2nd | 6/5/2 | −3.40 | .0040 | 1.09 |
| 2nd | 6/6/2 | −3.32 | .0041 | 1.69 |

Regarding separation potentials, the data shows that using different filters prior to calculation of the first derivative maximum, as well as prior to calculation of the second derivative maximum, there exist similar separation potentials with respect to criterium b) and sufficient separation potentials for all filters tested with respect to criterium c).

For determining the maximum of the first derivative, comparatively low CV (%) values have been obtained for all tested filter parameters. For determining the maximum of the second derivative, vertical window parameters of 6/2/b are identified as preferable, wherein b is either 3, 4, or 5.

EXAMPLE 3

Figure 5:
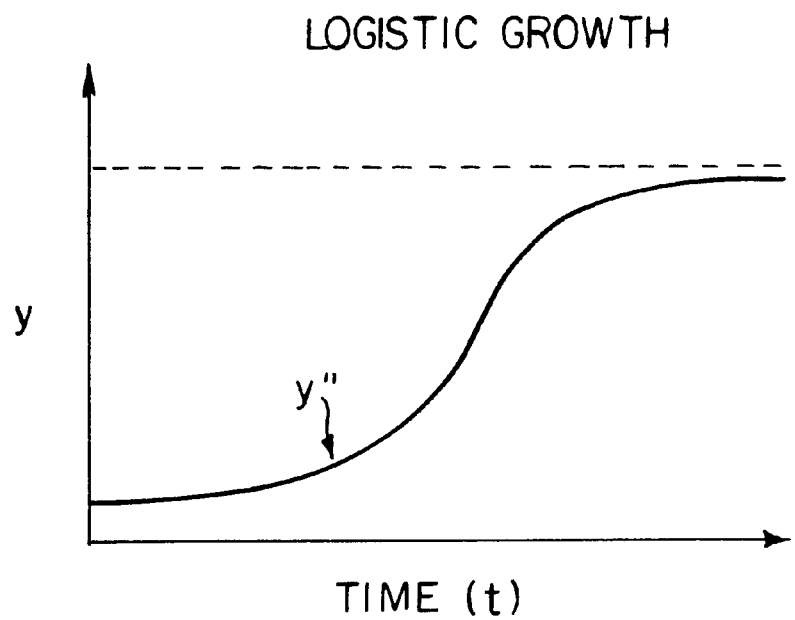
FIG. 5: Graphic representation of a logistic growth curve representative of the growth of a population of cells.

Logistic growth curves can be used to model population growth (FIG. 5). Such curves have a beginning lag phase, an exponential growth phase, and a plateau phase. Bacterial growth follows this kind of a curve. The effect of a stimulating or inhibiting compound on growth rate can be determined by following the relative number of organisms over time. If the curve shifts to the left, the compound is an inhibitor, if it shifts to the right, the compound stimulates growth. The potency of inhibition or stimulation is related to how far the curve shifts.

For example, a growth medium (LB broth) in a spectrophotometer cuvette is inoculated with a bacteria (*E. coli*), stirred and kept at 37° C. Every 5 minutes, bacterial growth is monitored by the light scatter through the cuvette at 500 nm. As the number of bacteria increase, the absorbance increases, giving a relative measure of the number of bacteria. The second derivative maximum is calculated to give a fractional cycle number of the control sample (T).

Figure 6:
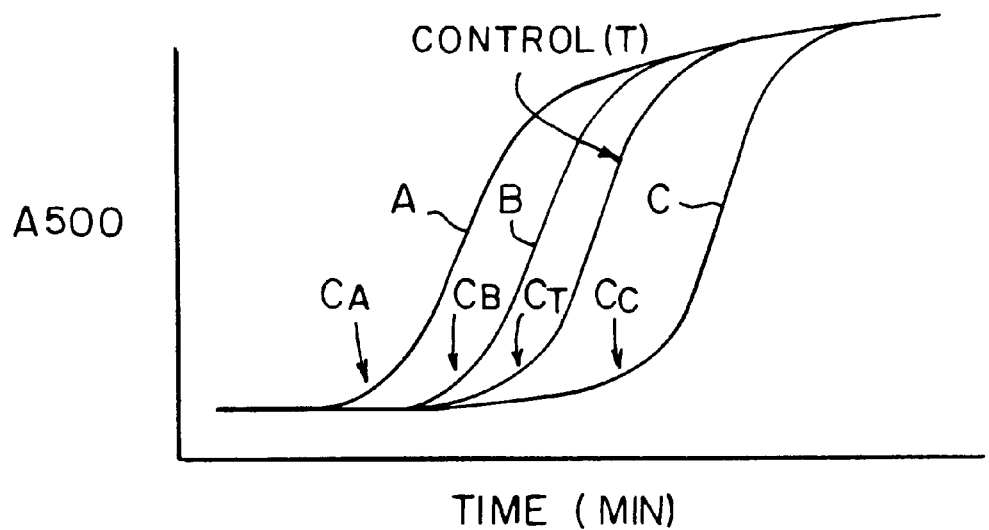

In parallel reactions, substances A, B, and C are added to separate cuvettes with media and inoculated as before. Their growth is monitored over time as above. Curves such as shown in FIG. 6 will be obtained. As indicated in the demonstrative data of FIG. 6, substance A is a more potent inhibitor than substance B, while substance C is a stimulator. The potency of inhibition can be quantified by the magnitude and direction of the shift in fractional cycle number:

$C_T$-$C_B$=magnitude of inhibition of substance B
$C_T$-$C_A$=magnitude of inhibition of substance A
$C_T$-$C_C$=magnitude of inhibition of substance C In addition to measuring the turbidity of the media (as measured at 500 nm) to assess growth, it should be clear that many other monitors of growth can be used, including pH shifts of the media or consumption of a nutrient. The only requirement is that a relative measure of population size is obtained sufficient to calculate derivatives.

What is claimed is:

1. A method for quantification of the concentration of a nucleic acid in a nucleic acid sample, comprising the steps of:

a) contacting said nucleic acid sample with an amplifying agent;

b) amplifying at least one predetermined locus of the nucleic acid in said nucleic acid sample by a process comprising the step of subjecting the sample to a number of amplification cycles to create a nucleic acid amplification product;

c) determining a value proportional to the amount of the nucleic acid amplification product present at each amplification cycle and using the values to generate a function;

d) calculating the first, second or n th order derivative of said function, wherein n is a positive integer;

e) determining a fractional cycle number corresponding to a maximum or minimum of said derivative; and f) calculating from said maximum or minimum an initial concentration of the nucleic acid in said nucleic acid sample.

2. The method of claim 1 wherein the amplifying agent comprises a pair of primers and a polymerase, and amplification occurs by polymerase chain reaction.

3. The method of claim 1, wherein during a progressive phase of amplification the amount of amplification product increases progressively and wherein after said progressive phase, the rate of amplification decreases.

4. The method of claim 1, wherein the value proportional to the amount of the amplification product is determined during an exponential phase of the amplification.

5. The method of claim 1, wherein the amplification product is detected by a double-stranded DNA binding entity.

6. The method of claim 1, wherein the amplification product is detected by means of fluorescence.

7. The method of claim 6 wherein the amplification product is detected by two polynucleotide probes, each labeled with a fluorescent entity, such that when both probes are hybridized to one strand of the nucleic acid amplification product, fluorescence resonance energy transfer occurs between the two fluorescent entities.

8. The method of claim 6, wherein the amplification product is detected by at least one fluorescently labeled polynucleotide probe, the sequence of which is identical with or complementary to the sequence of the amplification product over a range of at least 10 contiguous residues.

9. The method of claim 1 wherein the step of calculating the first, second or n th order derivative of said function comprises calculating the first derivative.

10. The method of claim 1 wherein the step of calculating the first, second or n th order derivative of said function comprises calculating the second derivative.

11. The method of claim 1 further comprising the step of
g) obtaining a standard curve generated using steps a–e on a plurality of additional nucleic acid samples having known concentrations of the nucleic acid; and wherein step f) comprises determining an initial concentration of the nucleic acid in said nucleic acid sample using the standard curve.

12. The method of claim 1 wherein the function is generated by performing a polynomial fit.

13. The method of claim 12 wherein the polynomial fit is calculated using a Savitzky Golay filter.

14. The method of claim 13 wherein the first, second or n th derivative is the first derivative, and the Savitzky Golay filter includes vertical window parameters 3/3/4.

15. The method of claim 13 wherein the first second or n th derivative is the second derivative, and the Savitzky Golay filter includes vertical window parameters 6/2/4.

16. A method for quantification of the concentration of a nucleic acid in a nucleic acid sample, comprising the steps of:
a) contacting said nucleic acid sample with an amplifying agent;
b) amplifying at least one predetermined locus of the nucleic acid in said nucleic acid sample by a process comprising the step of subjecting the sample to a number of amplification cycles to create a nucleic acid amplification product;
c) determining a value corresponding to the amount of the nucleic acid amplification product present at each amplification cycle and using the values to generate a function;
d) calculating an n th order derivative of said function, wherein n is a positive integer;
e) determining a fractional cycle number corresponding to a zero value of said derivative, said zero value corresponding to an extremum of an (n-1)th derivative of said function;
f) calculating from said zero value an initial concentration of the nucleic acid in said nucleic acid sample.

17. A method for quantification of the concentration of a nucleic acid in a nucleic acid sample, comprising the steps of:
a) contacting said nucleic acid sample with an amplifying agent;
b) amplifying at least one predetermined locus of the nucleic acid in said nucleic acid sample by a process comprising the step of subjecting the sample to a number of amplification cycles to create a nucleic acid amplification product;
c) determining a value corresponding to the relative amount of the nucleic acid amplification product present at each amplification cycle, to generate a data set;
d) generating a function from said data set;
e) calculating an n th order derivative of said function, wherein n is a positive integer;
f) determining a fractional cycle number corresponding to a maximum or minimum of said n th derivative;
g) obtaining a standard curve generated using steps a–e on a plurality of additional nucleic acid samples, each additional sample having a known concentration of the nucleic acid; and
h) determining an initial concentration of the nucleic acid in said nucleic acid sample using the standard curve.

18. The method of claim 17 wherein the function is generated by performing a polynomial fit.

19. The method of claim 18 wherein the polynomial fit is calculated using a Savitzky Golay filter.

20. The method of claim 19 wherein the n th derivative is the first derivative, and the Savitzky Golay filter includes vertical window parameters 3/3/4.

21. The method of claim 19 wherein the n th derivative is the second derivative, and the Savitzky Golay filter includes vertical window parameters 6/2/4.

22. A method for quantification of the concentration of a nucleic acid in a nucleic acid sample, comprising the steps of:
a) contacting said nucleic acid sample with an amplifying agent;
b) amplifying at least one predetermined locus of the nucleic acid in said nucleic acid sample by a process comprising the step of subjecting the sample to a number of amplification cycles to create a nucleic acid amplification product;
c) determining a value corresponding to the relative amount of the nucleic acid amplification product present at each amplification cycle, to generate a data set;
d) generating a function from said data set;
e) calculating an n th order derivative of said function, wherein n is a positive integer;
f) determining a fractional cycle number corresponding to a zero value of said n th derivative, said zero value corresponding to a maximum or minimum of an (n-1)th derivative of said function;
g) obtaining a standard curve generated using steps a–e on a plurality of additional nucleic acid samples, each additional sample having a known concentration of the nucleic acid; and
h) determining an initial concentration of the nucleic acid in said nucleic acid sample using the standard curve.

* * * * *